(12) United States Patent
Sirotka, II et al.

(10) Patent No.: US 11,872,439 B2
(45) Date of Patent: Jan. 16, 2024

(54) RESISTIVE SKATE DEVICE

(71) Applicant: Revathletic LLC, Houston, TX (US)

(72) Inventors: Michael Robert Sirotka, II, Houston, TX (US); Mary Descant Caldwell, Houston, TX (US)

(73) Assignee: Revathletic LLC, Houston, TX (US)

( * ) Notice: Subject to any disclaimer, the term of this patent is extended or adjusted under 35 U.S.C. 154(b) by 38 days.

(21) Appl. No.: 17/138,070

(22) Filed: Dec. 30, 2020

(65) Prior Publication Data
US 2022/0203156 A1 Jun. 30, 2022

(51) Int. Cl.
*A63B 21/00* (2006.01)
*A63B 21/04* (2006.01)
(Continued)

(52) U.S. Cl.
CPC ...... *A63B 21/4015* (2015.10); *A63B 21/0442* (2013.01); *A63B 21/0557* (2013.01);
(Continued)

(58) Field of Classification Search
CPC ............ A63B 21/0442; A63B 21/0557; A63B 21/4015; A63B 21/4009; A63B 21/00058; A63B 21/00061; A63B 21/00065; A63B 21/00185; A63B 21/04; A63B 21/0421; A63B 21/0428; A63B 21/0435; A63B 21/055; A63B 21/0552; A63B 21/0555; A63B 21/4025; A63B 69/0022; A63B 2102/24; A63B 2244/183;
(Continued)

(56) References Cited

U.S. PATENT DOCUMENTS

| | | | | |
|---|---|---|---|---|
| 2,097,376 A | * | 10/1937 | Marshman | A63B 21/0004 482/124 |
| 4,259,793 A | | 4/1981 | Morgan, Jr. et al. | |
| | | (Continued) | | |

FOREIGN PATENT DOCUMENTS

DE 202020101002 3/2020

OTHER PUBLICATIONS

PCT International Application No. PCT/US21/62743, International Search Report and Written Opinion of the International Searching Authority, dated Feb. 24, 2022, 10 pages.

*Primary Examiner* — Megan Anderson
(74) *Attorney, Agent, or Firm* — DLA PIPER LLP (US)

(57) ABSTRACT

A resistive training device to be worn by a user can include a first and second skate device configured to be worn on the user's feet. The first and second skate device can include a first plurality of attachment mechanisms. The first plurality of attachment mechanisms can include an interior attachment mechanism; an exterior attachment mechanism; and a rear attachment mechanism. The resistive training device can also include a belt configured to be worn around the user's waist. The belt can include comprising a second plurality of attachment mechanisms which can include a left hip attachment mechanism; a right hip attachment mechanism; and a tailbone attachment mechanism. The resistive training device can also include a plurality of resistive elements. Each resistive element can be removably connected to one of the first plurality of attachment mechanisms and one of the second plurality of attachment mechanisms.

18 Claims, 14 Drawing Sheets

(51) Int. Cl.
*A63B 21/055* (2006.01)
*A63B 69/00* (2006.01)
*A63B 102/24* (2015.01)
*A61F 5/01* (2006.01)

(52) U.S. Cl.
CPC ...... *A63B 21/4009* (2015.10); *A63B 69/0022* (2013.01); *A61F 5/0111* (2013.01); *A63B 21/00061* (2013.01); *A63B 21/4025* (2015.10); *A63B 2102/24* (2015.10); *A63B 2244/183* (2013.01); *A63B 2244/186* (2013.01); *A63B 2244/19* (2013.01)

(58) Field of Classification Search
CPC .......... A63B 2244/186; A63B 2244/19; A63B 22/20; A63B 22/203; A63B 23/0405
See application file for complete search history.

(56) References Cited

U.S. PATENT DOCUMENTS

| | | | |
|---|---|---|---|
| 5,186,701 A * | 2/1993 | Wilkinson | A63B 21/00065 482/121 |
| 5,203,754 A * | 4/1993 | Maclean | A63B 21/4015 482/121 |
| 5,303,940 A | 4/1994 | Brandner | |
| 5,647,827 A * | 7/1997 | Gutkowski | A63B 21/4025 482/122 |
| 5,690,595 A | 11/1997 | Quinones | |
| 5,813,955 A * | 9/1998 | Gutkowski | A63B 21/4007 482/121 |
| 6,202,263 B1 * | 3/2001 | Harker | B62J 7/08 2/237 |
| 6,551,221 B1 * | 4/2003 | Marco | A63B 69/0059 280/600 |
| 7,004,892 B2 | 2/2006 | Marco | |
| 7,618,356 B1 | 11/2009 | Johnson et al. | |
| 9,415,254 B2 * | 8/2016 | Dyer | A63B 21/0442 |
| 9,498,691 B2 * | 11/2016 | Antoine | A63B 21/4009 |
| 2002/0068667 A1 * | 6/2002 | Strachan | A63B 21/4025 482/125 |
| 2005/0059537 A1 | 3/2005 | Hull | |
| 2005/0282689 A1 * | 12/2005 | Weinstein | A63B 21/0552 482/121 |
| 2009/0183347 A1 | 7/2009 | Abels | |
| 2014/0073496 A1 | 3/2014 | Bannerman | |
| 2015/0335937 A1 * | 11/2015 | Park | A63B 21/4043 482/121 |
| 2016/0101309 A1 * | 4/2016 | Schreiber | A63B 21/0442 482/124 |
| 2018/0304134 A1 | 10/2018 | Parque | |

* cited by examiner

RESISTIVE SKATE DEVICE

TECHNICAL FIELD

The present disclosure relates to an exercise device that a person can use to improve physical conditioning and training via applications of resisted skating motions.

BACKGROUND OF THE DISCLOSURE

Various attempts have been made at designing devices that employ resistance-themed training for movements. For example, U.S. Pat. No. 5,203,754 to Maclean discloses a variable resistance leg harness exercise apparatus that includes a belt, foot and leg attachments, and stretchable cords that connect the belt and the foot and leg attachments. The objective of Maclean is to enable a user to perform under an increased load while not changing the user's natural center of gravity and without distorting the natural patterns of the exercise being performed. Notably, Maclean requires attachments to the knee, as well as the ankle. The device of Maclean is not suited for skating applications or connection to any type of skate as the knee connection would hinder proper knee bending such that a person would have an unnecessarily difficult time skating.

U.S. Patent Publication No. 2005/0059537 to Hull discloses a belt assembly that can be worn around the torso of a person, an adjustable foot and ankle portion, and a resilient connecting member (e.g., a resistance cord). Hull makes no suggestion of its applicability to skating motions; in fact, Hull also would be unlikely to be operable in conjunction with skates. As the connection utilizes a strap mechanism that slides around the foot, the possibility of slippage, instabilities during motion, potential disconnection from the foot, and the significant chance of injury resulting therefrom is too high from a safety perspective.

U.S. Patent Publication No. 2018/0304134 to Parque discloses a belt assembly that can be worn around the torso of a user that attaches to a stirrup worn around the ankle or foot of a user via a resistance cord or band. Once again, the stirrup is meant to slide over the user's foot with a strap or over the user's shoe with a strap. Parque suffers from similar deficiencies to Hull above, namely the instability and increased slippage from the simple stirrup/strap mechanism on the user's feet. In addition, Parque is limited to a single leg and is not designed to be used during moving exercises, let alone any gliding exercises. The device of Parque is designed as a "batting aid," in which a baseball player would wear the device while taking batting practice.

Finally, U.S. Pat. No. 7,004,892 to Marco discloses a training device for a gliding sport athlete that includes a belt and a pair of foot attachments. The foot attachments, similar to the other references mentioned above, includes a strap that sliders over a user's shoe or skate, incorporating the risks and instabilities as described above. In addition, Marco is explicitly limited to resistive cord connections to the belt at the front of the user's body (e.g., the lower abdomen above the groin area) and disparages the suitability of connections to the back for sliding or skating applications.

SUMMARY

According to one aspect of the present disclosure, a resistive training device to be worn by a user can include a first and second skate device configured to be worn on the user's feet that include a first plurality of attachment mechanisms; a belt configured to be worn around the user's waist that includes a second plurality of attachment mechanisms; and a plurality of resistive elements. The first plurality of attachment mechanisms can include an interior attachment mechanism; an exterior attachment mechanism; and a rear attachment mechanism. The second plurality of attachment mechanisms can include a left hip attachment mechanism; a right hip attachment mechanism; and a tailbone attachment mechanism. Each resistive element can be configured to be removably connected to one of the first plurality of attachment mechanisms and one of the second plurality of attachment mechanisms.

In some embodiments, each of the second plurality of attachment mechanisms can include at least one of a D-ring or an O-ring. In some embodiments, each of the first plurality of attachment mechanisms can include an anchor riveted or drilled to the associated skate device. In some embodiments, the anchor can be configured to hold a D-ring in a rotatable state. In some embodiments, each of the first plurality of attachment mechanisms can include at least one grommet.

In some embodiments, each of the plurality of resistive elements can include a carabiner clasp at each end. In some embodiments, each of the plurality of resistive elements can include a rubber material configured to slide over the carabiner clasp. In some embodiments, the skate device can include at least one of a three-wheel inline skate, a four-wheel inline skate, a hockey skate, a speed skate, a quad skate, or an ice-skate. In some embodiments, each of the plurality of resistive elements can be wrapped in cloth. In some embodiments, the plurality of resistive elements can include resistive elements with a plurality of lengths. In some embodiments, the plurality of resistive elements can include resistive elements with a plurality of tensile strengths. In some embodiments, the belt can include at least one of neoprene or linen.

According to another aspect of the present disclosure, a resistive training device to be worn by a user can include a first and second boot configured to be worn on the user's feet that include a first plurality of attachment mechanisms; a belt configured to be worn around the user's waist that includes a second plurality of attachment mechanisms; and a plurality of resistive elements. The first plurality of attachment mechanisms can include an interior attachment mechanism; an exterior attachment mechanism; and a rear attachment mechanism. The second plurality of attachment mechanisms can include a left hip attachment mechanism; a right hip attachment mechanism; and a tailbone attachment mechanism. Each of the plurality of resistive elements can be configured to be removably connected to one of the first plurality of attachment mechanisms and one of the second plurality of attachment mechanisms.

In some embodiments, each of the second plurality of attachment mechanisms can include at least one of a D-ring or an O-ring. In some embodiments, each of the first plurality of attachment mechanisms can include an anchor riveted or drilled to the associated boot. In some embodiments, the anchor can be configured to hold a D-ring in a rotatable state. In some embodiments, each of the first plurality of attachment mechanisms can include at least one grommet.

In some embodiments, each of the plurality of resistive elements can include a carabiner clasp at each end. In some embodiments, each of the plurality of resistive elements can include a rubber material configured to slide over the carabiner clasp. In some embodiments, the boot can include at least one of a snowboarding boot, a ski boot, a water-skiing boot, a wakeboarding boot, an athletic shoe, or a medical rehabilitation boot.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

The drawings are not necessarily to scale, or inclusive of all elements of a system, emphasis instead generally being placed upon illustrating the concepts, structures, and techniques sought to be protected herein.

DETAILED DESCRIPTION

Embodiments of the present disclosure relate to a resistive skate device for skating and other glide-motion training exercises. The resistive skate device can include a belt to be worn around the lower torso or waist of a user, two skates to be worn on the user's feet, and multiple resistive bands (referred to herein as elastic bands, resistance bands, resistive cords, etc.) that can attach to the belt and the skates. The resistive device can include various customizable connection points on both the skates and the belt, allowing the user to change the level and direction of resistance while training. The examples shown herein include an inline skating application and a hockey skate application, although these are non-limiting. For example, the resistive skate device of the present disclosure could be easily adapted to operate with ice-skates, roller skates, quad skating, skiing and snowboarding boots and/or bindings, medical rehabilitation boots, and/or other athletic shoes. Benefits of the disclosed resistive training skate device can include improved muscular strength and endurance. The skate device can be used to perform cardiovascular and anaerobic workouts in a low-impact but high-intensity manner. The nature of the disclosed resistive skate device allows for limited pressure and force exerted on the joint, while still allowing a person to significantly increase their heartrate and exert muscular effort. While particular benefits can be seen with respect to skating and gliding sports, the disclosed device can also provide complimentary training and performance benefits to athletes of other sports, such as soccer, football, basketball, track and field, etc., and even non-athletes with focuses on pure training, physical conditioning, and fitness.

Figure 1:
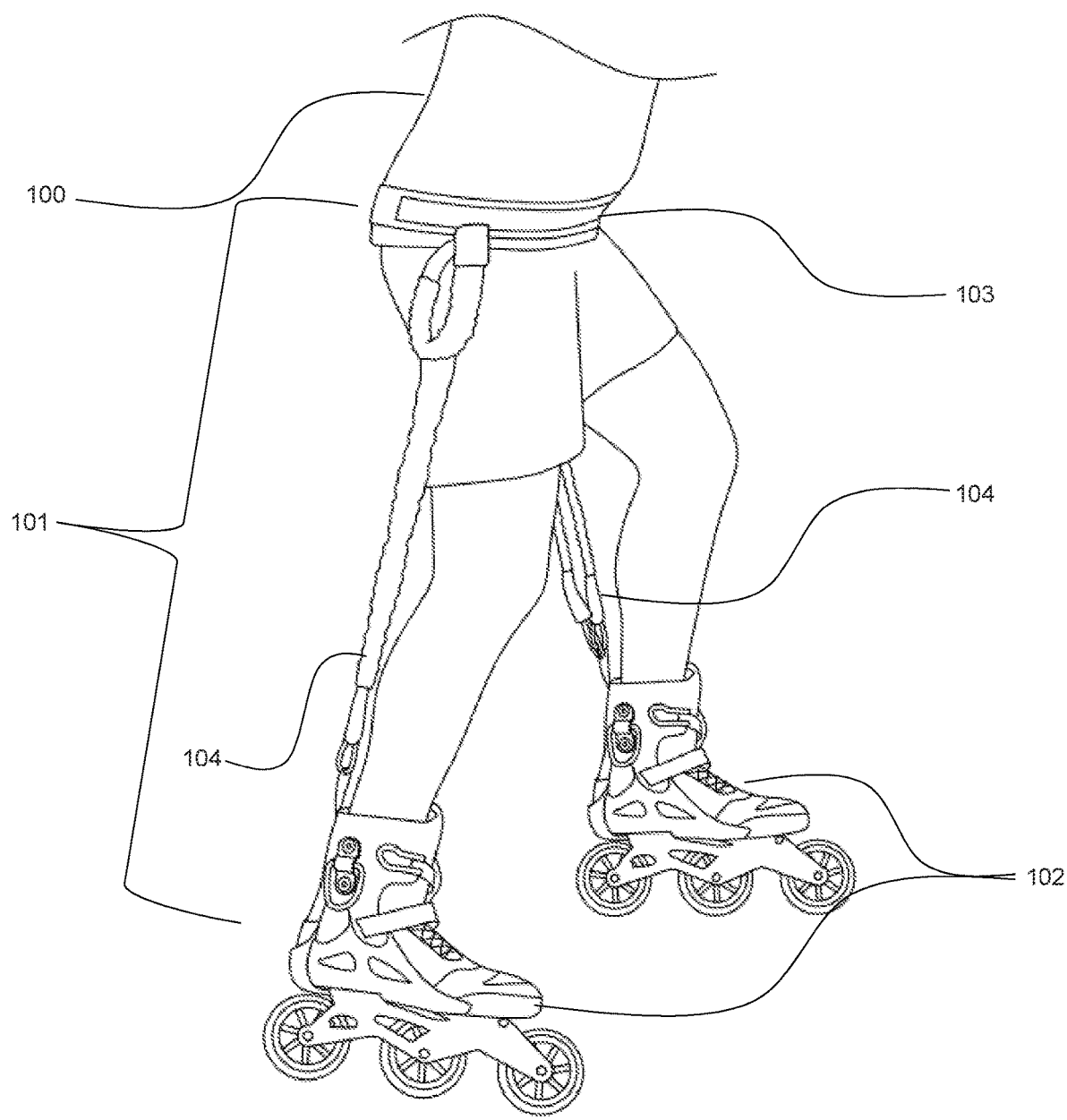
FIG. 1 shows an example of a person in motion while wearing a resistive skate device, according to some embodiments of the present disclosure.

FIG. 1 shows an example of a person 100 in motion while wearing a resistive skate device 101, according to some embodiments of the present disclosure. Person 100 can be skating while wearing the resistive skate device 101, which can serve to develop both a person's cardiovascular potential and muscular performance. Resistive skate device 101 can include skates 102, a belt 103, and resistive elements 104, which can herein be described as bungee cords, resistive cords or bands, and/or elastic members. In some embodiments, each resistive element can include a piece of rubber that closes off any connection points at each end (e.g., slides over the clasps). In some embodiments, each resistive element can be covered or wrapped in cloth. In some embodiments, the device, when purchased, can include resistive elements 104 with various resistance levels (e.g., different tensile strengths and/or lengths) to give a user flexibility in the strenuousness of an exercise. The skates 102 include three-wheel inline skates, although many others are possible, such as 4-wheel inline, speed skates, hockey skates, and ski/snowboarding boots and/or bindings. The resistive elements 104 can be attached at each end to the belt 103 and the skates 102. The details of the connection will be discussed later on in this disclosure. As the person 100 skates, the resistive elements 104 are in a stretched state and exhibits a downward pulling force on the belt 103 and thus the person 100's hip. The resistive elements 104 also exhibit an upward pulling force on the skates 102 and thus the person 100's feet. As a result, and in order to actually skate along and move, the person 100 would then need to exhibit opposite forces in the upward and downward directions, respectively, to maintain the resistive elements 104 in a stretched state. The exertion of forces to maintain the stretched-ness of the resistive elements provides a muscular workout for the person 100. In addition, maintaining this exertion over time, while skating, can provide a cardiovascular workout, as well as constant resistive tension on a user's muscles.

Figure 2:
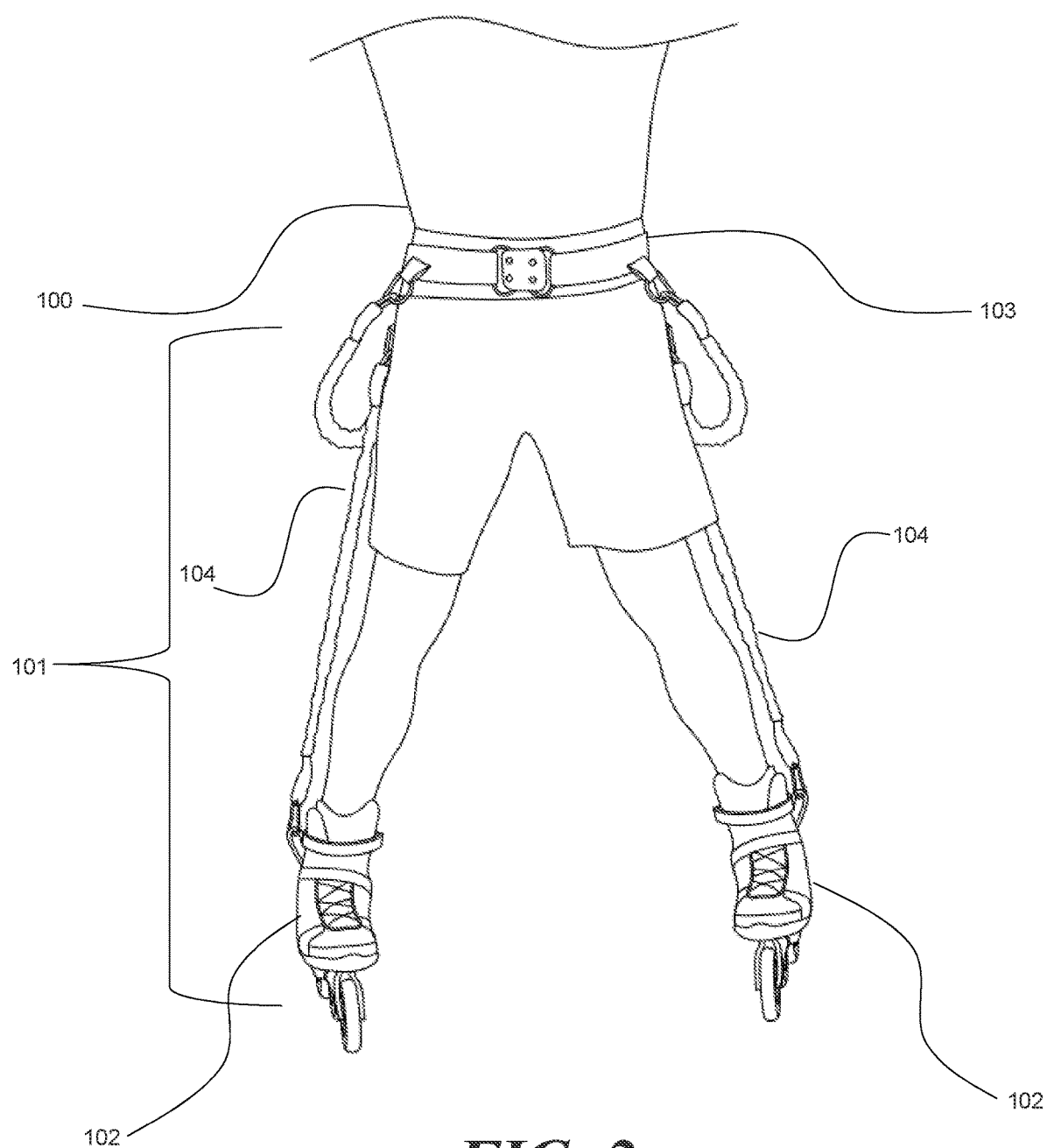
FIG. 2 shows a front view of a person wearing a resistive skate device, according to some embodiments of the present disclosure.

FIG. 2 shows a front view of the person 100 wearing a resistive skate device 101, according to some embodiments of the present disclosure. Similar to FIG. 1 above, the resistive skate device 101 can include skates 102 (e.g., inline skates), a belt 103 worn around the waist of the user 100, and resistive elements 104. The resistive elements 104 are attached to the belt 103 and the skates 102.

Figure 3:
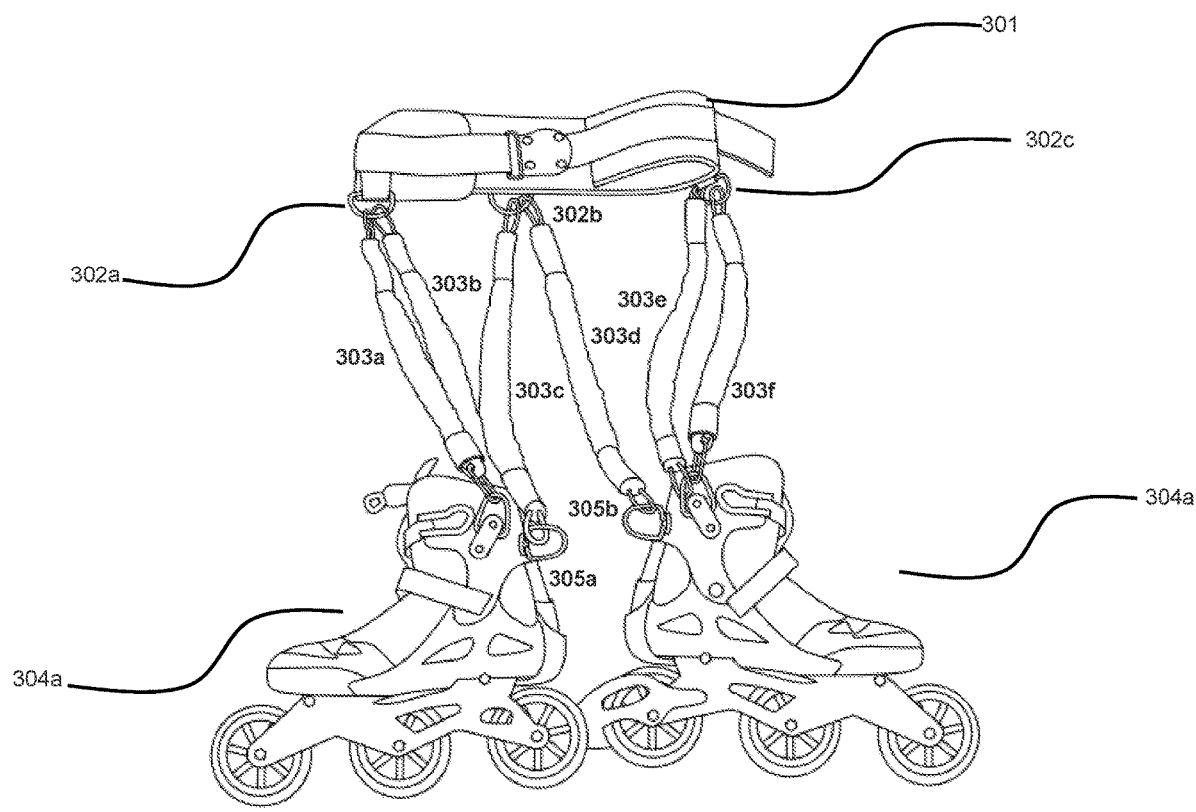
FIG. 3 shows a resistive skate device, according to some embodiments of the present disclosure.

FIG. 3 shows a resistive skate device 300, according to some embodiments of the present disclosure. The resistive skate device 300 can include a belt 301, resistive elements 303a-f (303 generally), and skates 304a-b. In some embodiments, the belt 301 can be made of neoprene or other similar materials and, when worn, can sit slightly above the hips of a user. In some embodiments, the belt 301 can be secured around the user's waist and/or hips via Velcro straps, a typical belt buckle (e.g., such as in a weight-lifting belt or a regular every-day belt), or other mechanism. In some embodiments, the tightness of the belt 301 can be adjusted to ensure a comfortable fit. The belt 301 can include three attachment points 302a-c. Attachment point 302a can reside at the right hip of a user, attachment point 302b can reside at the back (e.g., at about the tailbone) of a user, and the attachment point 302c can reside at the left hip of a user. Each attachment point 302 can include a D-ring (e.g., a stainless-steel D-ring or an O-ring) configured to connect to a resistive element 303. In some embodiments, the D-ring of each attachment point 302 can be connected through a piece of material that forms a loop extending from the belt. This configuration can allow rotation and movement of the D-rings without causing discomfort to the user; the configuration can also allow for a full range of motion for the user without hindering or sacrificing the ability to move in a fluent manner while exercising with the device 300. It is important to note that either D-rings or O-rings can be used herein.

While device 300 includes six resistive elements 303a-f, this number is merely exemplary in nature. The device 300 can include any number of resistive elements according to a user's preferences. One of the benefits of the resistive device of the present disclosure is the ability to customize the resistance of the device. For example, there can be multiple lengths and multiple tensile strengths of the resistive elements 303, providing a number of combinations for a user to take advantage of. Each resistive element 303 can include a clasp on either end; the clasp can be configured to be pressed by a user, allowing the clasp to be connected to the attachment point 302 (e.g., the D-ring) of the belt 301. In some embodiments, each skate 304 can include attachment mechanisms 305, which are described in greater detail in FIGS. 4-7. Each attachment mechanism 305 can be configured to receive and connect to a resistive element 303. In some embodiments, skates 304 can include three-wheel inline skates (as shown in FIG. 3), four-wheel inline skates, ice-skates, hockey, skates, quad skates, snowboarding boots, ski boots, water-ski boots, wakeboarding boots, athletic shoes, cross country boots, speed skates, and the like.

Figure 4A:
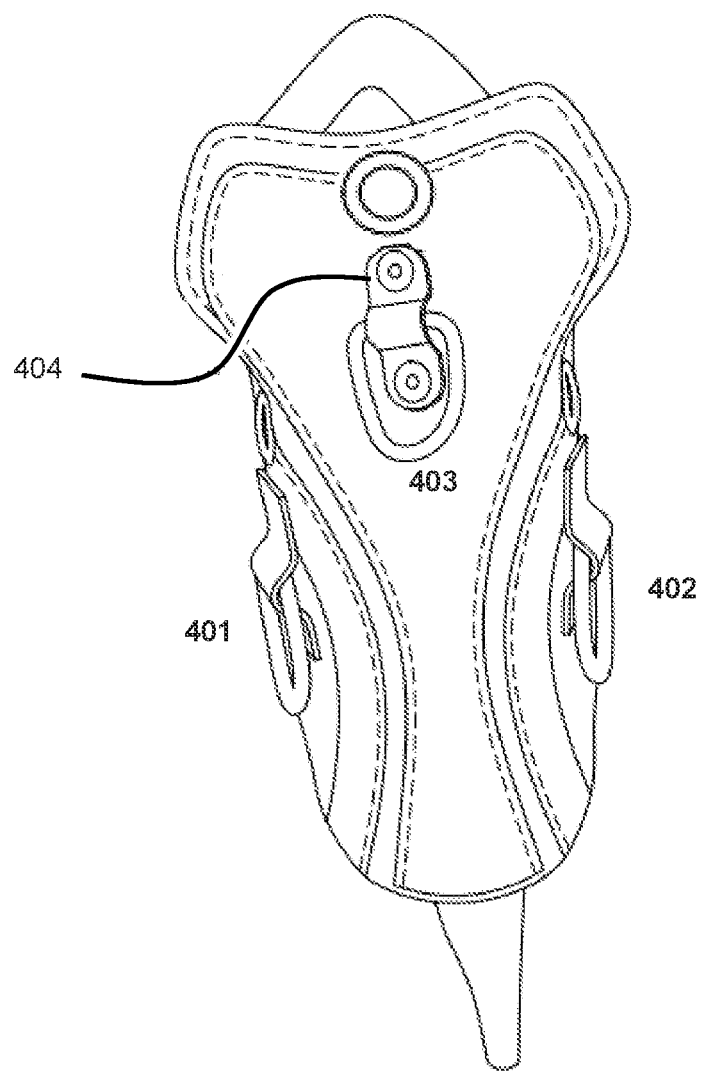
FIG. 4A shows a back view of a hockey boot that can be included in a resistive skate device, according to some embodiments of the present disclosure.

FIG. 4A shows a back view of a hockey boot 400 that can be included in a resistive skate device, according to some embodiments of the present disclosure. Hockey boot 400, which can also be described as a hockey skate, can include attachment mechanisms 401, 402, and 403. attachment mechanism 401 can reside on the left side of the boot 400, attachment mechanism 402 can reside on the right side of the boot 400, and attachment mechanism 403 can reside on the back of the boot 400. If boot 400 was a left-footed boot, then the attachment mechanism 401 would be designated as an "exterior attachment," connecting to the outside of the foot, while the attachment mechanism 402 would be designated as an "interior attachment," connecting to the inside of the foot. The opposite would be true if the boot were worn on a right foot. Each attachment can be configured to receive a clasp, such as a carabiner clasp. In this way, each attachment mechanism can be attached to the boot 400. For example, the boot can include an anchor, one on each side and one on the back or rear (anchor 404). Additionally or alternatively, a grommet can be used to attach the boot to a resistive element. The anchor 404 can facilitate connection between the attachment mechanism 403 and the boot 400. The attachment mechanism 403 then can be configured to receive and connect to a resistive element, such as a resistive element 303 as described with respect to FIG. 4. In some embodiments, an anchor, such as anchor 404, can be replaced with a hole and grommet, and clasps can be connected via looping through the grommet.

Figure 4B:
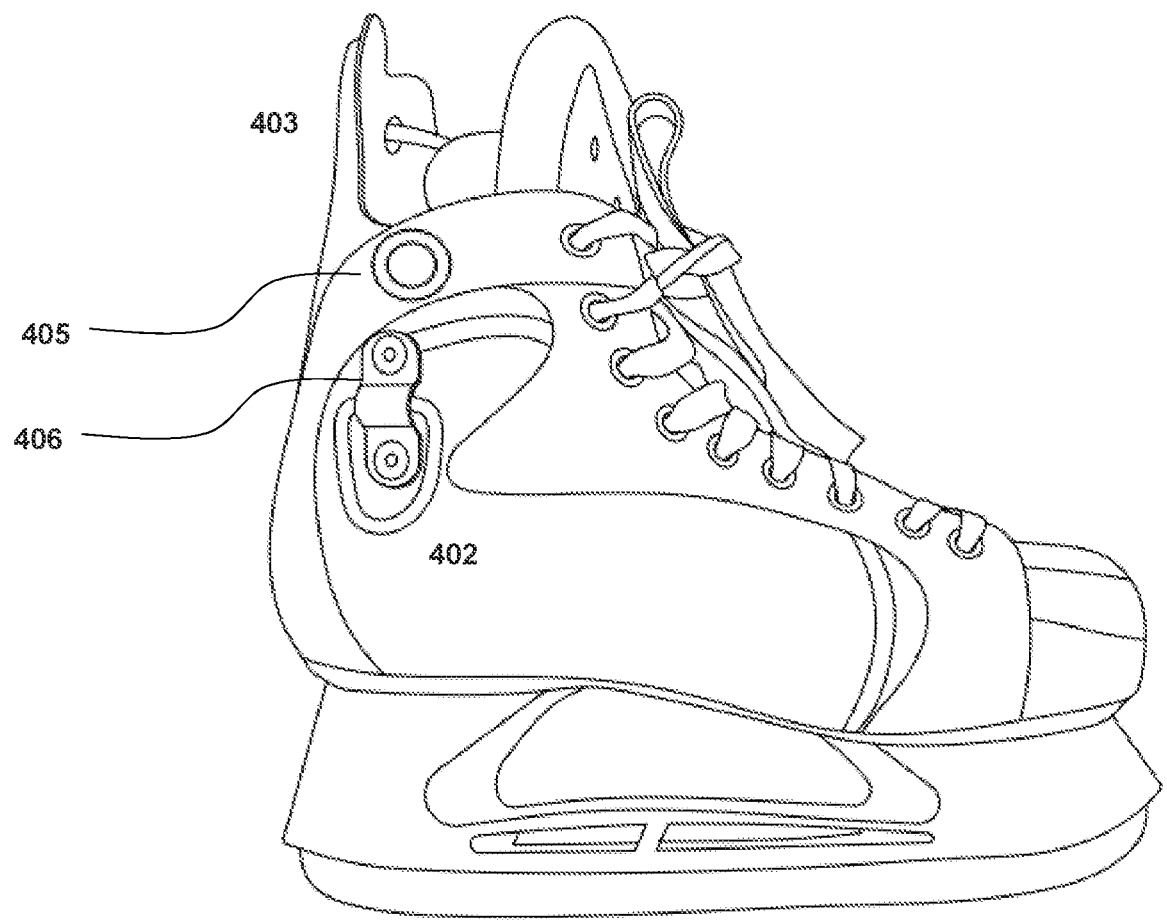
FIG. 4B shows a side view of a hockey boot that can be included in a resistive skate device, according to some embodiments of the present disclosure.

FIG. 4B shows a side view of a hockey boot 400 that can be included in a resistive skate device, according to some embodiments of the present disclosure. Similar to anchor 404 in FIG. 4A, side attachment mechanism 401 can be connected via anchor 406 that is created in the boot 400. In some embodiments, the boot 400 can include multiple grommets along the side of the boot (e.g., grommets 405) to allow for customization of the placement of the attachment mechanism and thus the placement of resistive elements. In some embodiments, a resistive element can attach directly to a grommet on a boot 400, without the need for the carabiner clasp mechanism, if preferred by a user.

Figure 5:
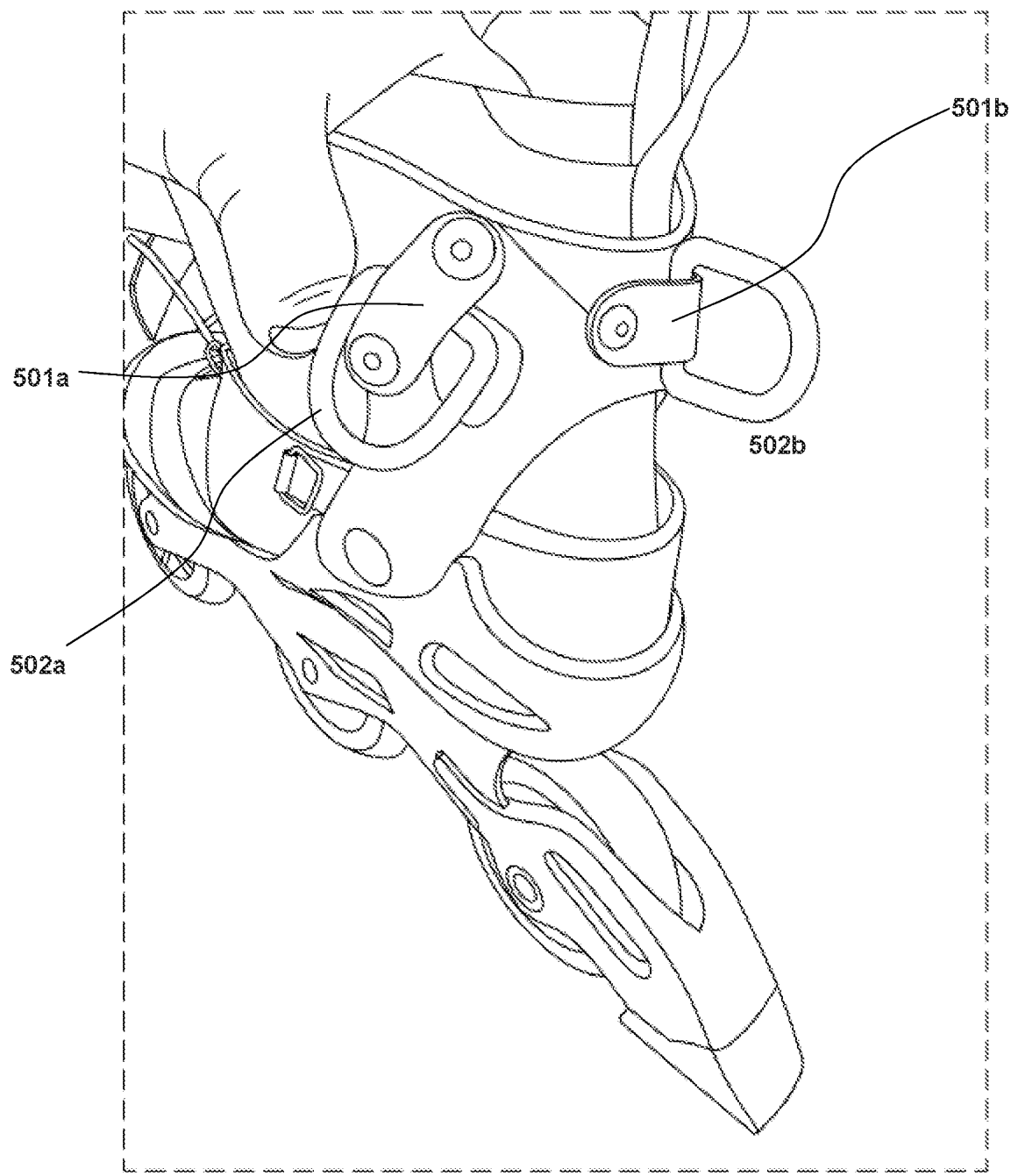
FIG. 5 shows a perspective view of an inline skate that can be included in a resistive skate device, according to some embodiments of the present disclosure.

FIG. 5 shows a perspective view of an inline skate 500 that can be included in a resistive skate device, according to some embodiments of the present disclosure. Inline skate 500 can include a plurality of anchors 501a-b (501 generally) on the left side and the back. In some embodiments, skate 500 can include a third anchor on the far side of the skate (not shown). Each anchor 501 can include an associated D-ring, such as D-rings 502a-b, to facilitate connection to an external clasp and thus a resistive element. Each anchor 501 can include two bolt or rivet connections to the skate 500 and a space or cavity between the bolts or rivets that is configured to receive a D-ring 502. In some embodiments, the cross-sectional area of the cavity and the D-ring 502 can be designed such that D-ring can rotate without excessive lateral motion. The possibility of D-ring rotation can increase the comfort level of the user while exercising. In some embodiments, as discussed above, each anchor 501 can alternatively be a grommet. In this example, each D-ring 502 would be looped through the grommet to facilitate connection.

Figure 6:
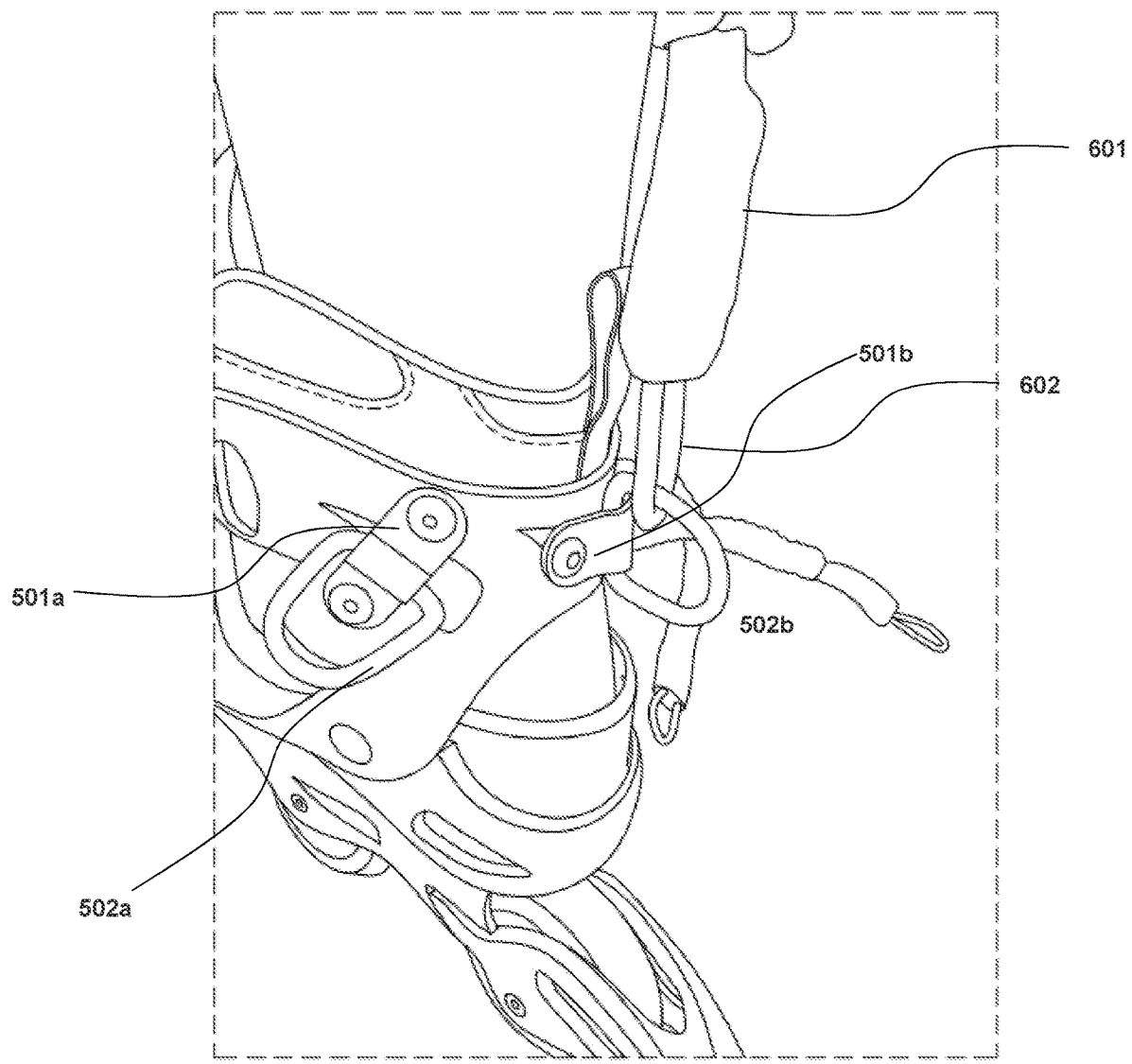
FIG. 6 shows a perspective view of an inline skate with resistance cord connections that can be included in a resistive skate device, according to some embodiments of the present disclosure.

FIG. 6 shows a perspective view of an inline skate 600 with resistance cord connections that can be included in a resistive skate device, according to some embodiments of the present disclosure. In some embodiments, the skate 600 of FIG. 6 can be the same as skate 500 of FIG. 5, with the addition of resistive element connections for use within an exercise routine. Similar to FIG. 5 above, skate 600 can include the same plurality of anchors 501a-b and associated D-rings 502a-b. In addition, skate 600 can include a resistive element 601 connected to the boot 600 via a clasp 602. The clasp 602 can be a carabiner clasp and can open in response to being pressed by a user. Once a user opens the clasp 602, it can be maneuvered such that it interlocks with the D-ring 502b and, when it is released, will close, completing the connection. As a user skates using skate 600, the resistive element 601 becomes stretched and can exert an upward force on the D-ring 502b and anchor 501b.

Figure 7:
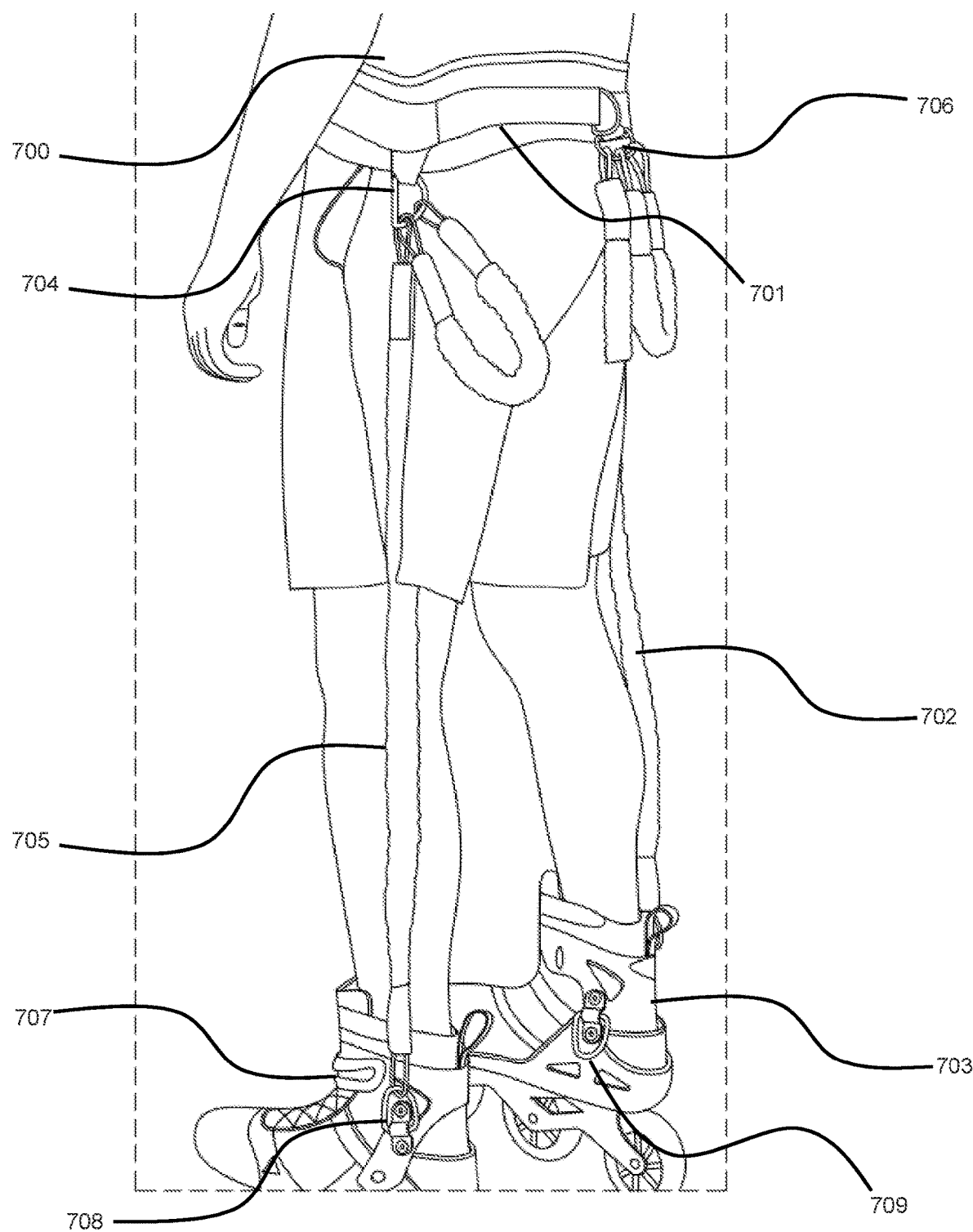
FIG. 7 shows a perspective view of a person wearing a resistive skate device with a hip to exterior connection, according to some embodiments of the present disclosure.

FIG. 7 shows a perspective view of a person 700 wearing a resistive skate device with a hip to exterior connection, according to some embodiments of the present disclosure. In some embodiments, person 700 can wear a belt 701 around their waist. The belt 701 can include various connection points, such as D-ring 704 (hip connection) and D-ring 706

(back connection). Belt 701 can also include a D-ring connection point on the opposite hip (not shown). According to embodiments of the present disclosure, the person 700 has the flexibility to choose which connection points along the belt to use based on their desired workout routine. The person 700 can decide whether they want the majority of the downward force on the belt to be concentrated at the hips, the back, or spread across both. In FIG. 7, the person 700 only employs hip connections via D-ring 704 and the unshown D-ring on the opposite hip.

D-ring 704 can be connected to a resistive element 705 via a carabiner clasp mechanism or other mechanism. The resistive element 705 can be connected on its opposite end to D-ring 708 located on skate 707, which can be referred to as an exterior connection. In addition, resistive element 702 (connected to the unshown D-ring on the person's 700 opposite hip) can be connected to the exterior anchor and connection point of the right boot 703. Boot 703 can also include an anchor and D-ring mechanism 709 on its interior, although it is unconnected in this example.

Figure 8:
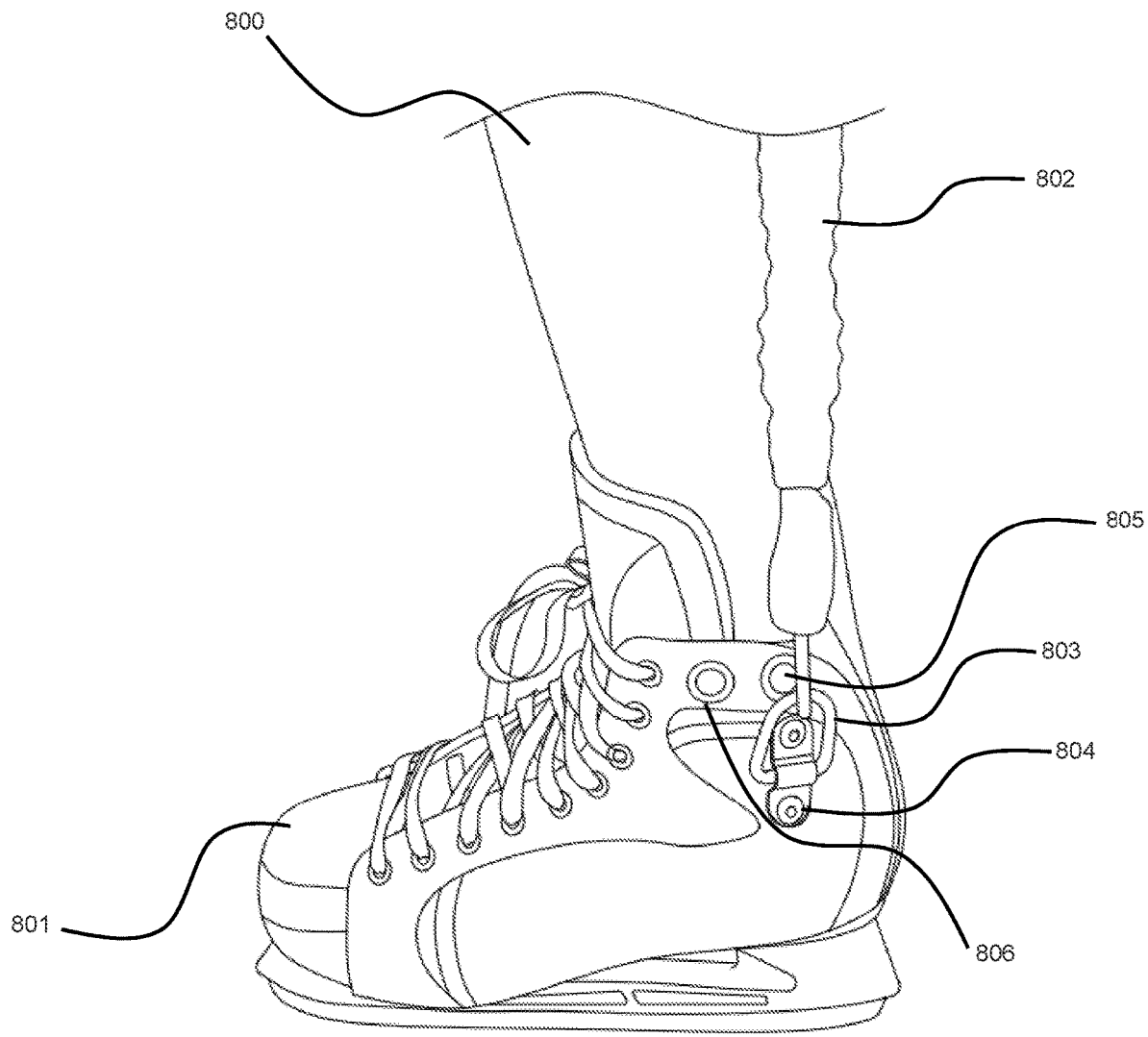
FIG. 8 shows a side view of a person wearing a resistive skate device with a hip to exterior connection, according to some embodiments of the present disclosure.

FIG. 8 shows a side view of a person wearing a resistive skate device with a hip to exterior connection, according to some embodiments of the present disclosure. In some embodiments, the view in FIG. 8 can be a closer view of the left leg of person 700 in FIG. 7. Person 800 can be wearing a boot 801 that is part of a resistive skate device, according to the present disclosure. Boot 801 can include a fastened anchor 804 configured to hold a D-ring 803. D-ring 803 can be configured to receive and connect to a resistive element 802 via a carabiner clasp or other clasping mechanism. In some embodiments, boot 801 can also include grommets 805 and 806, which can be used in place of the anchor 804 and D-ring 803. For example, the clasp of the resistive element 802 could clasp and connect directly to one of the grommets 805 or 806.

Figure 9:
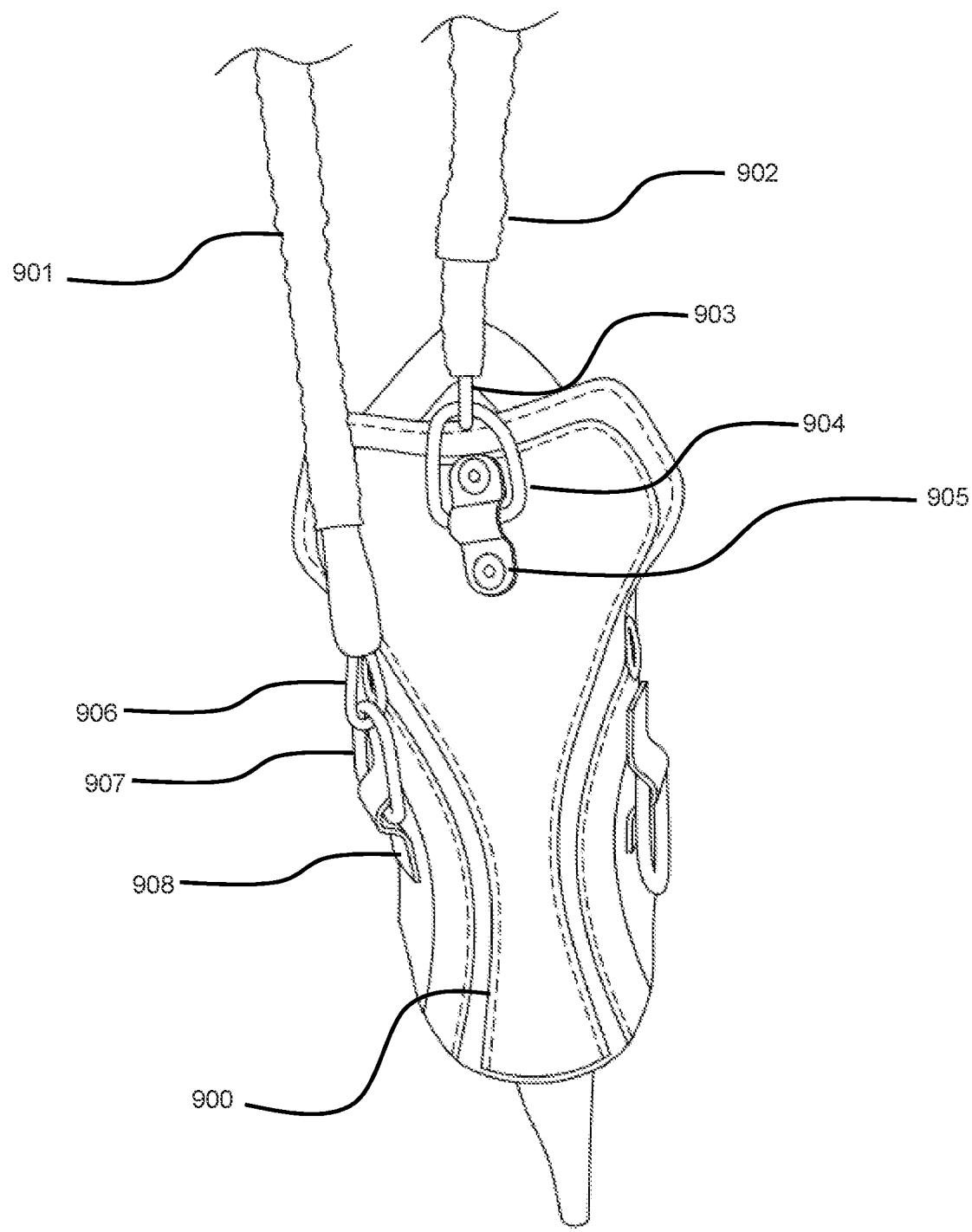
FIG. 9 shows a back view of a person wearing a resistive skate device, according to some embodiments of the present disclosure.

FIG. 9 shows a back view of a person wearing a resistive skate device, according to some embodiments of the present disclosure. In some embodiments, the skate device can include a skate 900 with one or more connections to a belt worn around a user's waist (not shown). Skate 900 can be connected to multiple resistive elements, elements 901 and 902. Resistive element 901 can be connected via clasp 906 to a D-ring 907 that is held by an anchor 908. In addition, resistive element 902 can be connected via clasp 903 to a D-ring 904 that is held by an anchor 905. When worn by a user, each of the resistive elements 901 and 902 can be in a stretched state and can exert an upward force on the boot. In order to counteract this upward force, the user would need to exert a downward force, which would require muscular exertion and thus serve as physical exercise.

Figure 10A:
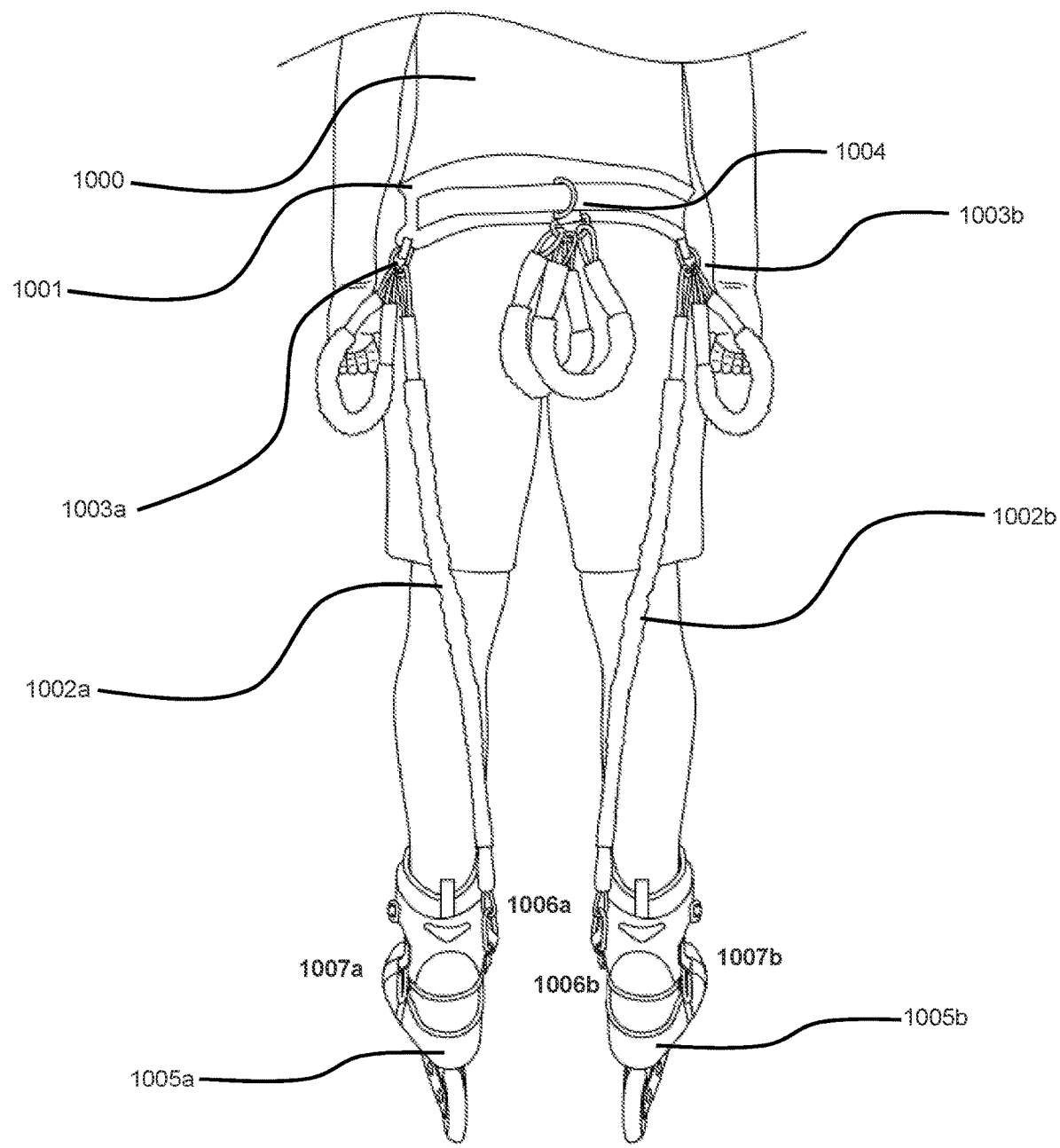
FIG. 10A shows a back view of a person wearing a resistive skate device with a hip to interior connection, according to some embodiments of the present disclosure.

FIG. 10A shows a back view of a person 1000 wearing a resistive skate device with a hip to interior connection, according to some embodiments of the present disclosure. Person 1000 can wear a belt 1001 around their waist. Belt 1001 can include various connection points (e.g., D-rings), two of which being located at the hip (1003a and 1003b) and one located at the tailbone or lower back (1004). In addition, the device can include skates 1005a and 1005b, each including both external anchor connections (1007a and 1007b) and internal anchor connections (1006a and 1006b). To facilitate a hip to interior connection, a resistive element 1002a can be connected, via clasp mechanisms, to D-ring 1003a on the belt 1001 and a D-ring held by anchor 1006a. Additionally, a resistive element 1002b can be connected, via clasp mechanisms, to D-ring 1003b on the belt 1001 and a D-ring held by anchor 1006b.

Figure 10B:
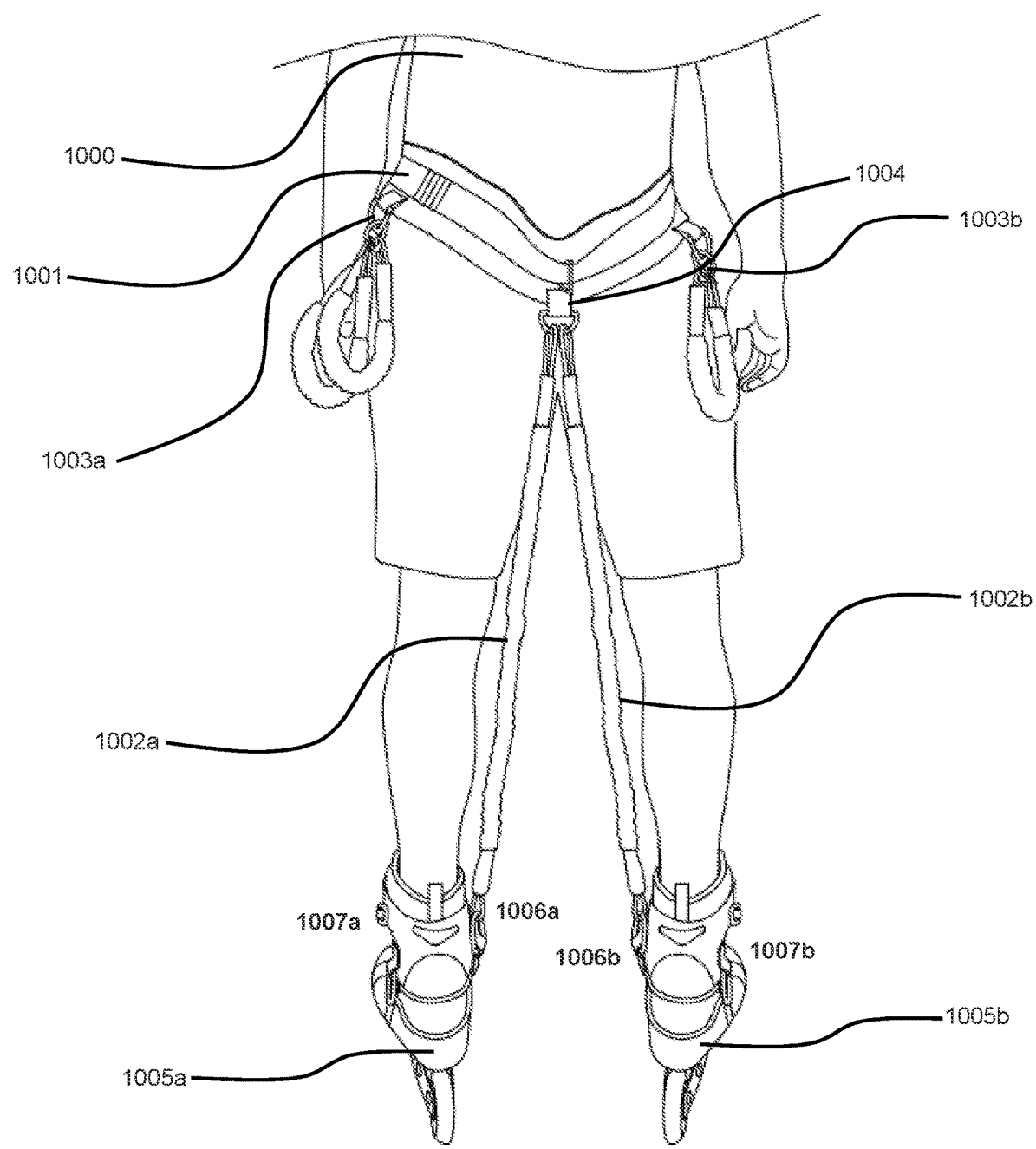
FIG. 10B shows a back view of a person wearing a resistive skate device with a back to interior connection, according to some embodiments of the present disclosure.

FIG. 10B shows a back view of a person 1000 wearing a resistive skate device with a back to interior connection, according to some embodiments of the present disclosure. Person 1000 can wear the same belt 1001 around their waist as FIG. 10A, as well as the same skates 1005a and 1005b. However, in FIG. 10B, which includes a back to interior connection, each of the resistive elements 1002a and 1002b can be connected with a clasp mechanism to D-ring 1004 located at the tailbone or lower back of the person 1000. The connections to the interior anchors of the boot, anchors 1006a and 1006b, can remain the same as in FIG. 10A.

Figure 10C:
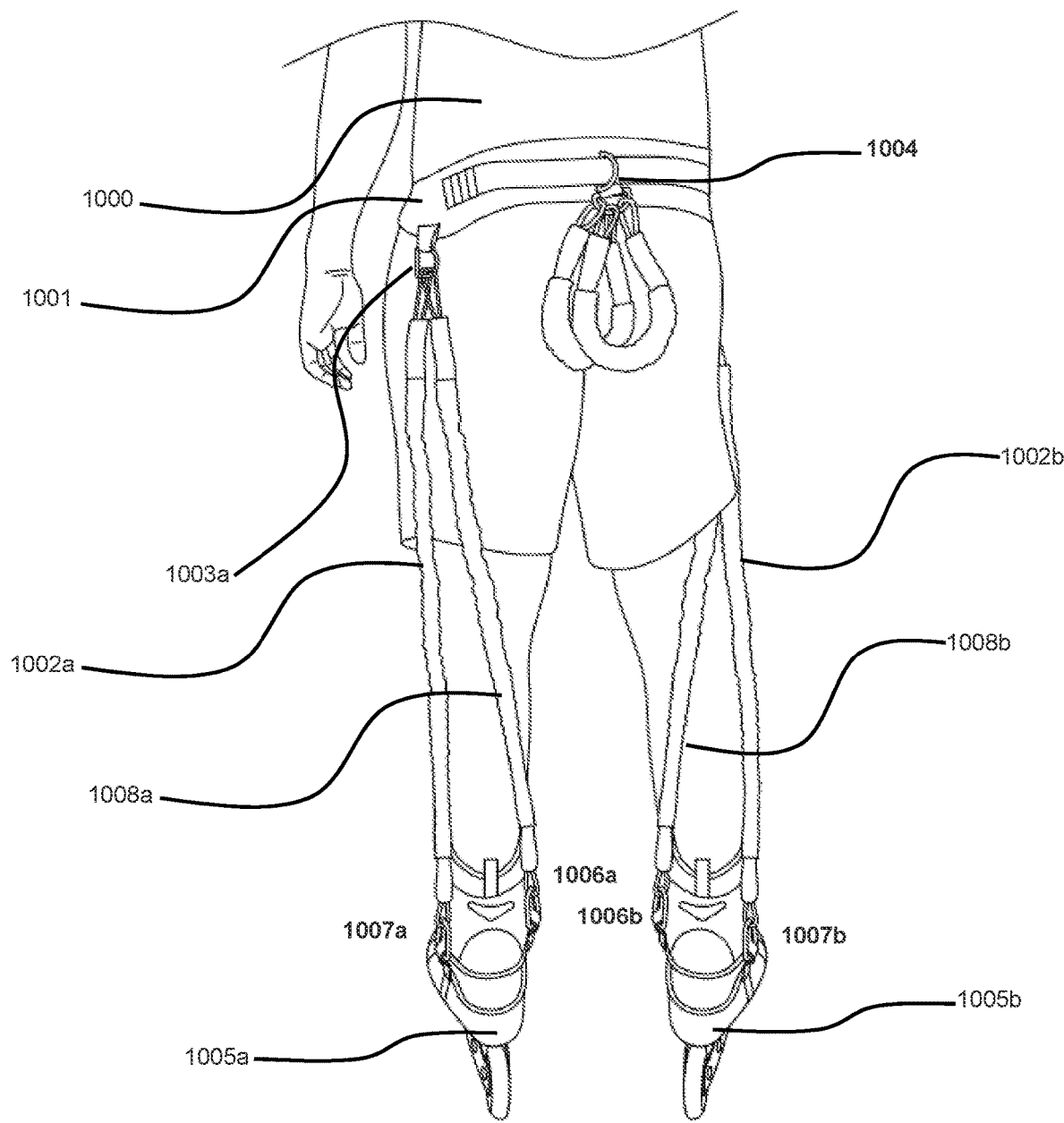
FIG. 10C shows a perspective view of a person wearing a resistive skate device with a hip to interior and hip to exterior connection, according to some embodiments of the present disclosure.

FIG. 10C shows a perspective view of a person 1000 wearing a resistive skate device with a hip to interior and hip to exterior connection, according to some embodiments of the present disclosure. Person 1000 can wear the same belt 1001 around their waist as FIGS. 10A and 10B, as well as the same skates 1005a and 1005b. However, in FIG. 10C, the person 1000 can utilize more than two resistive elements, or two or more on each side of the body. For example, on the left side of person 1000, two resistive elements 1002a and 1008a can be connected, via a clasp mechanism, to the same D-ring 1003a located at the left hip of the belt 1001. Resistive element 1002a can be connected to external anchor connection 1007a and resistive elements 1008a can be connected to internal anchor connection 1006a. On the right side of the person 1000, resistive elements 1002b and 1008b can both be connected, via a clasp mechanism, to a D-ring on the right hip of the person 1000 (not shown). Resistive element 1002b can be connected, via a clasp mechanism, to external anchor connection 1007b and resistive element can be connected, via a clasp mechanism, to internal anchor connection 1006b.

Figure 11:
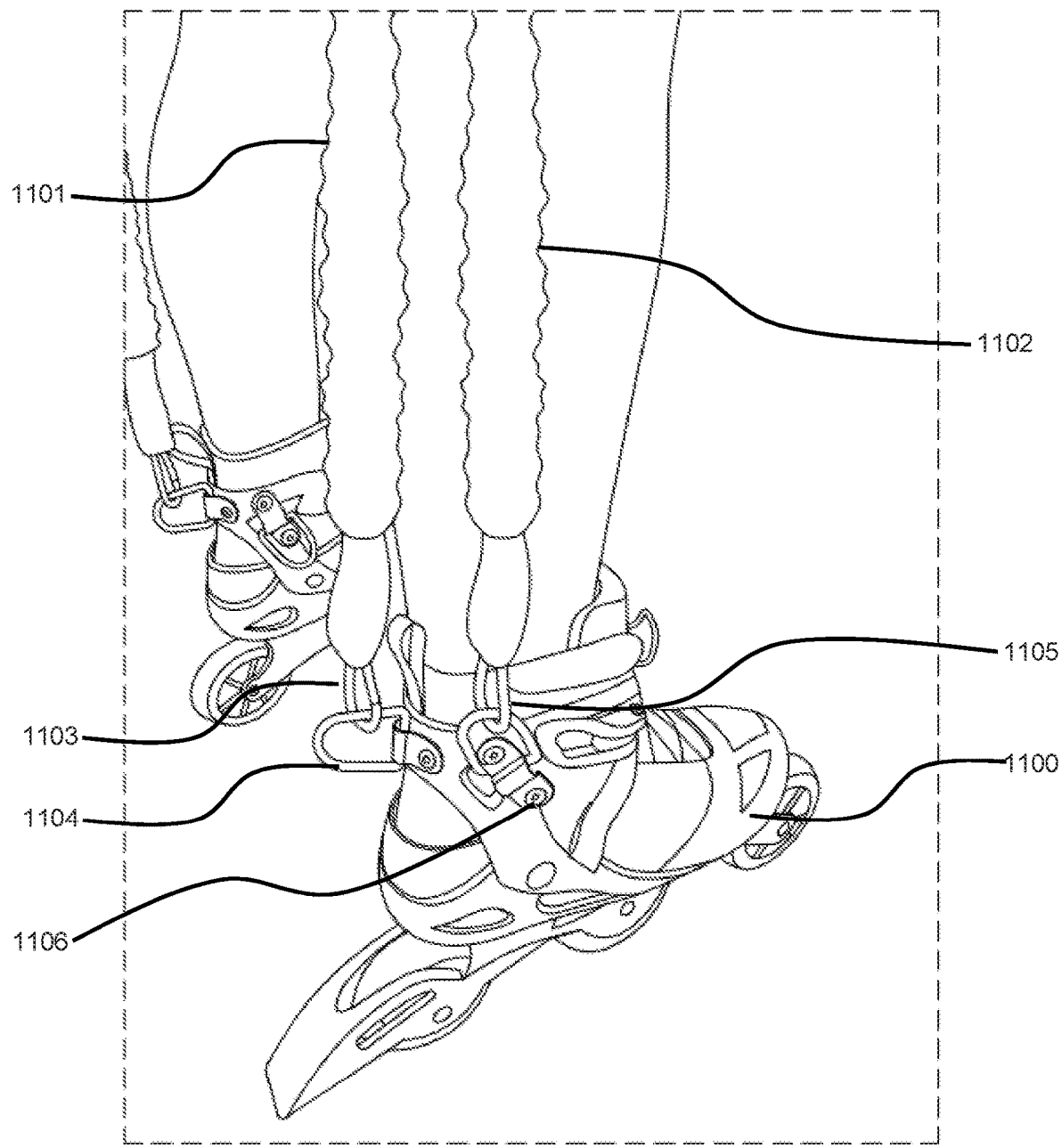
FIG. 11 shows a perspective view of a back and exterior inline connection, according to some embodiments of the present disclosure.

FIG. 11 shows a perspective view of a back and exterior inline connection, according to some embodiments of the present disclosure. A person's right skate 1100 can include an external anchor and D-ring mechanism 1106 that connects to clasp 1105 of resistive element 1102. In addition, the skate 1100 can include a back anchor and D-ring mechanism 1104 that connects to clasp 1103 of resistive element 1101. On their opposite ends (not shown), each of the resistive elements 1101 and 1102 can be connected to various parts of a belt as described herein, such as the hip or back.

While various embodiments have been described above, it should be understood that they have been presented by way of example and not limitation. It will be apparent to persons skilled in the relevant art(s) that various changes in form and detail may be made therein without departing from the spirit and scope. In fact, after reading the above description, it will be apparent to one skilled in the relevant art(s) how to implement alternative embodiments. For example, other steps may be provided, or steps may be eliminated, from the described flows, and other components may be added to, or removed from, the described systems. Accordingly, other implementations are within the scope of the following claims.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

Although the disclosed subject matter has been described and illustrated in the foregoing illustrative embodiments, it is understood that the present disclosure has been made only by way of example, and that numerous changes in the details of implementation of the disclosed subject matter may be made without departing from the spirit and scope of the disclosed subject matter.

The invention claimed is:

1. A resistive training device configured to be worn by a user comprising:
   a first and second skate device configured to be worn on the user's feet and comprising a first plurality of attachment mechanisms, the first plurality of attachment mechanisms each comprising:
      a first anchor fixed to the respective skate device at an inside of a respective ankle and comprising a first cavity configured to receive a first rotatable ring, wherein the first cavity is parallel to a bottom surface of the respective skate device and the first rotatable ring rotates about a first axis parallel to the bottom surface of the respective skate device;
      a second anchor fixed to the respective skate device at an outside of the respective ankle and comprising a second cavity configured to receive a second rotatable ring, wherein the second cavity is parallel to the bottom surface of the respective skate device and the second rotatable ring rotates about a second axis parallel to the bottom surface of the respective skate device; and
      a third anchor fixed to the respective skate device at a rear of the respective ankle and comprising a third cavity configured to receive a third rotatable ring, wherein the third cavity is perpendicular to the bottom surface of the respective skate device and the third rotatable ring rotates about an axis perpendicular to the bottom surface of the respective skate device;
   a belt configured to be worn around the user's waist and comprising a plurality of attachment mechanisms, the plurality of attachment mechanisms comprising:
      a left hip attachment mechanism positioned at a left hip of the user;
      a right hip attachment mechanism positioned at a right hip of the user; and
      a tailbone attachment mechanism positioned at a tailbone of the user; and
   a plurality of resistive elements, each being configured to be removably connected to one of the plurality of attachment mechanisms and one of the first, second, and third rotatable rings.

2. The resistive training device of claim 1, wherein each of the plurality of resistive elements comprises a carabiner clasp at each end.

3. The resistive training device of claim 2, wherein each of the plurality of resistive elements comprises a rubber material configured to slide over the carabiner clasp.

4. The resistive training device of claim 1, wherein each of the first, second, and third rotatable rings comprises one of a D-ring or an O-ring.

5. The resistive training device of claim 1, wherein each of the first, second, and third anchors is configured to hold a D-ring in a rotatable state.

6. The resistive training device of claim 1, wherein each of the first second, and third anchors comprises one grommet.

7. The resistive training device of claim 1, wherein each of the first and second skate device comprises a three-wheel inline skate, a four-wheel inline skate, a hockey skate, a speed skate, a quad skate, or an ice-skate.

8. The resistive training device of claim 1, wherein each of the plurality of resistive elements is wrapped in cloth.

9. The resistive training device of claim 1, wherein the plurality of resistive elements comprises resistive elements with a plurality of lengths.

10. The resistive training device of claim 1, wherein the plurality of resistive elements comprises resistive elements with a plurality of tensile strengths.

11. The resistive training device of claim 1, wherein the belt comprises at least one of neoprene or linen.

12. A resistive training device configured to be worn by a user comprising:
   a plurality of boots comprising a first and a second boot configured to be worn on the user's feet and comprising a first plurality of attachment mechanisms, the first plurality of attachment mechanisms each comprising:
      a first anchor fixed to the respective skate device at an inside of a respective ankle and comprising a first cavity configured to receive a first ring, wherein the first cavity is parallel to a bottom surface of the respective skate device and the first rotatable ring rotates about a first axis parallel to the bottom surface of the respective skate device;
      a second anchor fixed to the respective skate device at an outside of the respective ankle and comprising a second cavity configured to receive a second rotatable ring, wherein the second cavity is parallel to the bottom surface of the respective skate device and the second rotatable ring rotates about a second axis parallel to the bottom surface of the respective skate device; and
      a third anchor fixed to the respective skate device at a rear of the respective ankle and comprising a third cavity configured to receive a third rotatable ring, wherein the third cavity is perpendicular to the bottom surface of the respective skate device and the third rotatable ring rotates about an axis perpendicular to the bottom surface of the respective skate device;
   a belt configured to be worn around the user's waist and comprising a plurality of attachment mechanisms, the plurality of attachment mechanisms comprising:
      a left hip attachment mechanism positioned at a left hip of the user;

a right hip attachment mechanism positioned at a right hip of the user; and a tailbone attachment mechanism positioned at a tailbone of the user; and a plurality of resistive elements, each being configured to be removably connected to one of the plurality of attachment mechanisms and one of the first, second, and third rings.

13. The resistive training device of claim 12, wherein each of the plurality of resistive elements comprises a carabiner clasp at each end.

14. The resistive training device of claim 13, wherein each of the plurality of resistive elements comprises a rubber material configured to slide over a respective carabiner clasp.

15. The resistive training device of claim 12, wherein each of the first, second, and third rings comprises one of a D-ring or an O-ring.

16. The resistive training device of claim 12, wherein each of the first, second, and third anchors is configured to hold a D-ring in a rotatable state.

17. The resistive training device of claim 12, wherein each of the first second, and third anchors comprises one grommet.

18. The resistive training device of claim 12, wherein each of the first and second boots comprise one of a snowboarding boot, a ski boot, a water-skiing boot, a wakeboarding boot, an athletic shoe, or a medical rehabilitation boot.

\* \* \* \* \*